United States Patent [19]

Takahashi et al.

[11] Patent Number: 4,897,507
[45] Date of Patent: Jan. 30, 1990

[54] METHOD FOR PRODUCING α-L-ASPARTYL-L-PHENYLALANINE DERIVATIVES

[75] Inventors: Satoji Takahashi; Tadashi Takemoto, both of Yokkaichi, Japan

[73] Assignee: Ajinomoto Co., Inc., Tokyo, Japan

[21] Appl. No.: 216,214

[22] Filed: Jul. 7, 1988

[30] Foreign Application Priority Data

Jul. 22, 1987 [JP] Japan ................................ 62-183199

[51] Int. Cl.⁴ ............................................. C07C 103/52
[52] U.S. Cl. ...................................................... 560/41
[58] Field of Search ........................................... 560/41

[56] References Cited

U.S. PATENT DOCUMENTS 4,634,790  1/1987  Shimohara et al. .................... 560/41
4,780,561 10/1988  Mita et al. ............................. 560/41

FOREIGN PATENT DOCUMENTS 2559773  8/1985  France .

*Primary Examiner*—Bruce Gray
*Attorney, Agent, or Firm*—Oblon, Spivak, McClelland, Maier & Neustadt

[57] ABSTRACT

A method for producing α-L-aspartyl-L-phenylalanine dimethyl ester, which comprises reacting 3-benzyl-6-carboxymethyl-2,5-diketopiperazine or methyl ester thereof in a methanolic solvent substantially free from water in the presence of a strong acid.

9 Claims, No Drawings

METHOD FOR PRODUCING α-L-ASPARTYL-L-PHENYLALANINE DERIVATIVES

BACKGROUND OF THE INVENTION

1. Field of the Invention

The present invention relates to a method for producing α-L-aspartyl-L-phenylalanine dimethyl ester which is an intermediate in the production of α-L-aspartyl-L-phenylalanine methyl ester and to a method for producing α-L-aspartyl-L-phenylalanine methyl ester from the dimethyl ester.

2. Description of the Background

α-L-Aspartyl-L-phenylalanine methyl ester (α-APM) is a substance that is much in demand as a novel low calorie sweetener of good quality.

For the production of α-APM, a variety of methods are already known. One method involves the condensation of N-protected-L-aspartic anhydride with L-phenylalanine methyl ester and the N-protective group is then cleaved in a conventional manner (U.S. Pat. No. 3,786,039). Another method is the direct condensation of a strong acid addition salt of L-aspartic anhydride with L-phenylalanine methyl ester (Published Examined Japanese Patent Application No. 14217/74) Still another method is the condensation of N-protected-L-aspartic acid with L-phenylalanine methyl ester in the presence of an enzyme. The N-protective group is then cleaved in a conventional manner (Published Examined Japanese Patent Application No. 135595/80).

However, α-APM tends to change to easily revert to 3-benzyl-6-carboxymethyl-2,5-diketopiperazine or, if α-APM is in a medium containing alcohol, it is partly converted into the alkyl ester (DKP or DKP derivatives), because of its physical properties. In the production of α-APM on an industrial scale, the yield of by-products is large. The problem of by-product formation is common to all of the methods for producing α-APM.

On the other hand, a method is known for producing α-APM in which a DKP or DKP derivative is brought into contact with a strong acid in a solvent mixture of methanol and water, thereby resulting in the cleavage of the amide bond (Published Unexamined Japanese Patent Application Nos. 174799/85 and 22519/86). According to the method, however, water is present in large quantities and the reaction is carried out using strong acids so that both of the peptide bonds in DKP are cleaved to the by-products: aspartic acid and phenylalanine. Further, also, in the case where one of the two peptide bonds in DKP is cleaved, the selectivity is poor and undesired phenylalanyl aspartic acid or the methyl ester thereof is produced in large quantities. A need therefore continues to exist for a method by which α-APM can be produced in improved yields from DKP with greatly reduced hydrolysis to the basic amino acid materials and undesired peptides.

SUMMARY OF THE INVENTION

Accordingly, one object of the present invention is to provide a method of preparing α-APM from DKP or derivatives thereof in improved yields while minimizing the production of undesired by-products including the starting amino acids.

Briefly, this object and other objects of the present invention as hereinafter will become more readily apparent can be attained by a method of producing α-L-aspartyl-L-phenylalanine methyl ester by reacting 3-benzyl-6-carboxymethyl-2,5-diketopiperazine or methyl ester thereof in a methanolic solvent substantially free from water in the presence of a strong acid.

DETAILED DESCRIPTION OF THE PREFERRED EMBODIMENTS

In the investigation leading to the present invention, it has been found that upon contact of the DKP or DKP derivative with a strong acid, cleavage of the peptide bonds unexpectedly occurs, even though water is not present. In addition, the cleavage of only one of the peptide bonds occurs with the amide bond on the aspartyl side being predominantly cleaved so that α-L-aspartyl-L-phenylalanine dimethyl ester, which is a compound wherein the aspartic acid residue of α-L-aspartyl-L-phenylalanine and the carboxyl residue of phenylalanine are converted into methyl esters (α-APM$_2$), is produced. Further, the α-APM$_2$ produced in this reaction system is extremely stable and can be very easily converted to α-APM (HCl), quite advantageously from an industrial viewpoint, by continuously contacting α-APM$_2$ with an aqueous solvent containing HCl and methanol. In the present invention, the cleavage reaction is discontinued with the cleavage of one of the peptide bonds in the DKP or DKP ester. In addition, α-APM$_2$ is extremely stable under the conditions of the present invention, though α-APM$_2$ is known to be a compound that is easily diketopiperazinated, saponified, and the like. Therefore, the industrial value of the present invention is quite substantial.

α-APM$_2$ obtained by the method of the present invention, can be easily converted to α-APM by known methods. In particular, when α-APM$_2$ is present in the aqueous solution containing HCl and methanol as disclosed in Published Unexamined Japanese Patent Application No. 129258/84, α-APM$_2$ can be converted into α-APM hydrochloride (α-APM.HCl) stably in high yield.

In the conversion of DKP or DKP methyl ester to α-AMP$_2$, the DKP and DKP methyl ester by-products prepared from α-APM are isolated and used. Alternatively, when they are dissolved or suspended in solutions of water or organic solvents, the solutions or suspensions may also be used by concentrating and replacing the solvent with methanol solvent. Further, DKP and DKP methyl esters synthesized by other methods may also be used. Still further, the presence of some α-APM or associated derivatives thereof in the solution of DKP does not adversely affect the reaction.

The solvent is methanol which does not contain significant amounts of water. In the case water is present, it is preferred that water be minimized as much as possible with the water content generally being 30 wt % or less, preferably 20 wt % or less, more preferably 15 wt % or less, based on the methanolic solvent. Suitable solvent mixtures with alcohols other than methanol, for example, alcohols such as ethanol, propanol, butanol, or the like, and further with aliphatic acid alkyl esters such as methyl acetate, ethyl acetate, etc. can also be used in the present invention. Further, solvent mixtures of the methanolic solvent with other organic solvents can also be used.

In the event the amount of solvent employed is insufficient, based on the amount of DKP or DKP methyl ester used, operations can only be conducted with difficulty. An amount exceeding a 6 mole ratio is generally preferred.

Any acid is usable in the cleavage reaction as long as it is a strong acid such as hydrochloric acid (including hydrogen chloride), sulfuric acid, hydrobromic acid, and the like. Hydrochloric acid and sulfuric acid are preferred. The amount of the acid used is generally within the range of 0.5 to 15 equivalents based on the DKP or DKP methyl ester, while the reaction proceeds with an amount of acid of 0.1 equivalent or more.

While the reaction rate varies depending upon the amount of the acid used, the reaction temperature is generally selected within the range of 0° to 150° C. It is not necessary to increase the temperature excessively, but a temperature of 10° to 80° C. is appropriate.

The reaction time is not particularly limited because the time period of completing the reaction varies depending upon the amount of the acid used. The reaction time is generally within a range of 0.1 to 20 hours.

It is possible to prepare α-APM in a conventional manner from the reaction solution containing the α-$APM_2$ which is formed. Inter alia, the following method is preferred from an industrial viewpoint. That is, when the solvent is removed by distillation from the reaction solution or an aqueous hydrochloric acid solution is added thereto as it is and the solution is stirred, α-AMP HCl precipitates. Thus, α-AMP.HCl is separated and if necessary, can be converted to free α-APM in a conventional manner.

The initial concentration of α-AP derivatives such as α-$APM_2$ in the APM.HCl crystallization step is generally from 5 to 70 g/dl. The concentration from 10 to 50 g/dl is suitable from an industrial aspect since high concentration causes high viscosity.

The HCl concentration in the crystallization liquid is ordinarily 2–8 M/l. Since a low concentration results in a low crystallization rate and a high concentration results in significant decomposition, the preferred concentration is 2–6 M/l.

The methanol concentration in the crystallization liquid is ordinarily 1–10 g/dl. Either low or high concentration of methanol causes a low crystallization rate of α-APM.HCl. The preferable concentration is 2–6 g/dl.

Further when the solvent is removed by distillation, for example, an aqueous sodium carbonate solution is added to the residue, free α-$APM_2$ is extracted with an organic solvent such as toluene, or the like, and α-$APM_2$ is extracted into the aqueous phase with an aqueous hydrochloric acid solution. APM.HCl then precipitates. The precipitate may be isolated.

As has been described above, in the present invention, α-APM and α-$APM_2$ can be produced in high yields by preventing the formation of by-products that have been the problem in the prior art. In the present method cleavage of the peptide bond of DKP or DKP esters occurs in the substantial absence of water. The α-$APM_2$ obtained can then be converted into α-APM. Thus, a method is provided of producing α-APM in greatly improved yield. The present invention is therefore a material contribution to the α-APM producing industry.

Having now fully described the invention, it will be apparent to one of ordinary skill in the art that many changes and modifications can be made thereto without departing from the spirit or scope of the invention as set forth herein.

EXAMPLE 1

To 26.2 g of 3-benzyl-6-carboxymethyl-2,5-diketopiperazine were added 500 ml of methanol and 40 ml of 98 wt % sulfuric acid. The mixture was heated to reflux for 2 hours with stirring. One milliliter of the reaction solution was subjected to sampling. Analysis by high performance liquid chromatography showed that 78.5% of α-APM2 was formed (based on 3-benzyl-6-carboxymethyl-2,5-diketopiperazine).

EXAMPLE 2

In 400 ml of methanol was suspended 26.2 g of 3-benzyl-6-carboxymethyl-2,5-diketopiperazine. An 18.3 g amount of HCl was then passed into the suspension followed by heating at reflux for 4 hours. One milliliter of the reaction solution was subjected to sampling. Analysis of the solution similar to the manner of Example 1 showed that 77.6% of α-$APM_2$ had formed (based on 3-benzyl-6-carboxymethyl-2,5-diketopiperazine).

EXAMPLE 3

To 1000 ml of methanol and 25.5 ml of 35 wt % hydrochloric acid was added 26.2 g of 3-benzyl-6-carboxymethyl-2,5-diketopiperazine. The mixture was stirred at 55° to 65° C. for 4 hours. One milliliter of the reaction solution was sampled. Analysis of the solution showed that 72.7% of α-APM2 had formed (based on 3-benzyl-6-carboxymethyl-2,5-diketopiperazine).

EXAMPLE 4

In 100 ml of methanol was dissolved 27.6 g of 3-benzyl-6-carboxymethyl-2,5-diketopiperazine. An 18.1 g amount of hydrogen chloride was passed into the solution followed by reaction at 65° C. for 4 hours. Analysis of the solution in the manner of Example 1 showed that α-$APM_2$ was produced in a yield of 79.0% (based on 3-benzyl-6-carboxymethyl-2,5diketopiperazine).

EXAMPLE 5

To 27.6 g of 3-benzyl-6-carboxymethyl-2,5-diketopiperazine were added 1.0 liter of methyl acetate and 35 ml of 98 wt % sulfuric acid. The mixture was heated at reflux for 10 hours with stirring. The yield of α-$APM_2$ in this reaction solution was 48.5%.

EXAMPLE 6

The whole volume of the reaction solution obtained in Example 2 was concentrated. After methanol was removed by distillation, 4.0 M/l of aqueous hydrochloric acid solution was added to bring the volume of the solution to 100 ml to adjust the methanol concentration in the solution to 4 g/dl. The solution was stirred at 20° C. for 8 days and then stirred at 3° to 5° C. for one day. The precipitated crystals were removed by filtration.

The obtained crystals were dissolved in water and an analysis for α-APM was conducted by high performance liquid chromatography. α-APM was obtained in an amount of 20.1 g.

EXAMPLE 7

The whole volume of the reaction solution obtained in Example 3 was treated in a manner similar to Example 6. α-APM was obtained in an amount of 19.3 g.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for producing α-L-aspartyl-L-phenylalanine methyl ester hydrochloride, which comprises:

reacting 3-benzyl-6-carboxymethyl-2,5-diketopiperazine or methyl ester thereof in a methanolic solvent containing water in an amount of 30 wt. % or less based on the solvent, in the presence of a strong acid thereby obtaining α-L-aspartyl-L-phenylalanine dimethyl ester; and then separately reacting the dimethyl ester in an aqueous solvent containing hydrochloric acid and methanol to produce α-L-aspartyl-L-phenylalanine methyl ester.

2. The method of claim 1, wherein said methanolic solvent, besides methanol, contains an alcohol or ester cosolvent.

3. The method of claim 1, wherein the amount of water in said methanolic solvent is less than 20 wt %.

4. The method of claim 1, wherein said strong acid is hydrochloric acid, sulfuric acid or hydrobromic acid.

5. The method of claim 1, wherein the amount of strong acid ranges from 0.5 to 15 equivalents per equivalent of said DKP or DKP methyl ester reactant.

6. The method of claim 1, wherein the reaction occurs at a temperature of 0° to 150° C.

7. The method of claim 1, wherein the concentration of hydrochloric acid in the second step ranges from 2-8 M/l.

8. The method of claim 7, wherein said HCl concentration ranges from 2-6 M/l.

9. The method of claim 1, wherein, when said α-L-aspartyl-L-phenylalanine methyl ester produced by hydrolysis is separated from its solution by precipitation, it precipitates from a methanol solution containing methanol in a concentration of 1-10 g/dl.

* * * * *